(12) United States Patent
Gonzales (10) Patent No.: US 7,431,717 B2
(45) Date of Patent: Oct. 7, 2008

(54) CENTRAL NERVOUS SYSTEM ADMINISTRATION OF MEDICATIONS BY MEANS OF PELVIC VENOUS CATHETERIZATION AND REVERSAL OF BATSON'S PLEXUS

(75) Inventor: Gilbert R. Gonzales, New York, NY (US)

(73) Assignee: Serene Medical, Inc., New York, NY (US)

( * ) Notice: Subject to any disclaimer, the term of this patent is extended or adjusted under 35 U.S.C. 154(b) by 363 days.

(21) Appl. No.: 10/675,147

(22) Filed: Sep. 30, 2003

(65) Prior Publication Data

US 2005/0070843 A1 Mar. 31, 2005

(51) Int. Cl.
*A61M 31/00* (2006.01)
(52) U.S. Cl. .................................... 604/507
(58) Field of Classification Search .......... 604/2, 604/500, 506–508, 517, 93.01, 131, 27, 28; 606/201

See application file for complete search history.

(56) References Cited

U.S. PATENT DOCUMENTS

| | | | |
|---|---|---|---|
| 467,599 | A | 1/1892 | Abundi et al. |
| 2,170,222 | A | 8/1939 | Strauss |
| 2,254,833 | A | 9/1941 | Ashkenaz |
| 2,491,274 | A | 10/1949 | McNeill |
| 3,126,006 | A | 3/1964 | Dowell |
| 3,324,855 | A | 6/1967 | Heimlich |
| 3,368,549 | A | 2/1968 | Barr et al. |
| 4,233,025 | A | 11/1980 | Larson et al. |
| 4,471,782 | A | 9/1984 | Shuffield |
| 4,516,578 | A | 5/1985 | Shuffield |
| 4,572,832 | A | 2/1986 | Kigasawa et al. |
| 4,925,327 | A | 5/1990 | Wirt |

(Continued)

FOREIGN PATENT DOCUMENTS

DE 2516350 10/1976

(Continued)

OTHER PUBLICATIONS

Oscar V. Batson, M.A., M.D., *The Function of the Vertebral Veins and Their Role in the Spread of Metastases*, Annals Surgery, 1940; 112:138-149.

(Continued)

*Primary Examiner*—Kevin C. Slrmons
*Assistant Examiner*—Catherine N Witczak
(74) *Attorney, Agent, or Firm*—Wood, Herron & Evans, L.L.P.

(57) ABSTRACT

An infusor system for administering medications to a venous blood vessel in the body of a patient. The infusor system includes a flexible, elongated delivery tube having opposite ends. One of the ends is couplable to a supply of liquid medication, which is remote from the venous blood vessel. The system further includes a delivery component coupled to the other end of the delivery tube. This delivery component is adaptable to be placed in confronting relationship with the venous blood vessel so that medication from said supply may be introduced directly into the venous blood vessel and distributed in the body of the patient. The infusor system further includes a pressure-altering device used for increasing intraabdominal pressure in the body of the patient. Sampling of venous blood from the meningorrhachidian vasculature is also possible.

13 Claims, 5 Drawing Sheets

U.S. PATENT DOCUMENTS

| | | | | |
|---|---|---|---|---|
| 4,941,875 | A | * | 7/1990 | Brennan ..................... 604/81 |
| 4,979,948 | A | | 12/1990 | Geddes et al. |
| 5,059,182 | A | | 10/1991 | Laing |
| 5,061,243 | A | * | 10/1991 | Winchell et al. ............ 604/132 |
| 5,123,431 | A | | 6/1992 | Wilson |
| 5,152,742 | A | | 10/1992 | Simpson |
| 5,158,532 | A | | 10/1992 | Peng et al. |
| 5,207,642 | A | | 5/1993 | Orkin et al. |
| 5,377,874 | A | | 1/1995 | Brown |
| 5,549,569 | A | * | 8/1996 | Lynn et al. .................. 604/191 |
| 5,830,186 | A | | 11/1998 | Gonzales et al. |
| 5,846,216 | A | * | 12/1998 | Gonzales et al. ............... 604/2 |
| 6,401,719 | B1 | * | 6/2002 | Farley et al. ................ 128/898 |
| 6,699,231 | B1 | * | 3/2004 | Sterman et al. ............ 604/509 |
| 2001/0049486 | A1 | * | 12/2001 | Evans et al. ................ 604/4.01 |
| 2002/0188253 | A1 | * | 12/2002 | Gordon et al. ......... 604/101.03 |
| 2008/0058768 | A1 | * | 3/2008 | Gonzales .................... 604/523 |

FOREIGN PATENT DOCUMENTS

| | | |
|---|---|---|
| EP | 0263976 | 4/1988 |
| EP | 0281212 | 7/1988 |
| WO | WO 81/00356 | 2/1981 |

OTHER PUBLICATIONS

James E. Eckenhoff, M.D., *The Physiologic Significance of the Vertebral Venous Plexus*, Surgery, Gynecology & Obstetrics, 1970; 131:72-76.

Wilson I.B. Onuigbo, *Batson's Theory of Vertebral Venous Metastasis, A Review*, Oncology, 32; 145-150/1975.

Gonzales et al., *Analgesia Using Vertebral Venous Plexus (Batson's Plexus) Shunting of Rectally Administered Opioids and Anesthetics to the Central Nervous System*, J. of Pain & Symptom Management, V. 7 No. 4, May 1992.

Ewoud J. van Hoogdalem et al., *Pharmacokinetics of Rectal Drug Administration, Part I: General Considerations and Clinical Applications of Centrally Acting Drugs*, Clin. Pharmacokinet 21/1C, Nov. 26, 1991.

Carla Ripamonti et al., *Rectal, Buccal, and Sublingual Narcotics for the Management of Cancer Pain*, J. of Palliative Care, 7: Jan. 1991; 30-35.

A.G. De Boer et al., *Drug Absorption by Sublingual and Rectal Routes*, Br. J. of Anesthesia, 1984, 56, 69.

Vasant V. Ranade, Ph.D. et al., *Drug Delivery Systems*, CRC Press, Boca Raton, 1996, 264-284.

* cited by examiner

CENTRAL NERVOUS SYSTEM ADMINISTRATION OF MEDICATIONS BY MEANS OF PELVIC VENOUS CATHETERIZATION AND REVERSAL OF BATSON'S PLEXUS

FIELD OF THE INVENTION

The present invention relates generally to the administration of medications to patients, and specifically, to the administration of medications through the venous system of a patient, and more specifically, through the superficial to sacral venous system of a patient.

BACKGROUND OF THE INVENTION

The effective administration of medications for the treatment of disease symptoms and for the alleviation of pain, i.e., pain management, is an important aspect to the overall treatment of patients for both curable diseases and terminal illnesses. Particularly, the effective administration of medications in patients experiencing chronic pain associated with a terminal illness is particularly important, because such pain management requires constant administration of medication over prolonged periods of time. As a result, the management of pain for terminally ill patients, such as terminal cancer and those afflicted with HIV, has come to the forefront as the medical profession seeks to alleviate pain to allow the patient to comfortably pass away.

Oral administration has been widely utilized in the past for dispensing pain medications such as narcotic and non-narcotic analgesics. However, oral administration is oftentimes not possible due to an obstruction blocking the oral and gastrointestinal tract, or due to severe nausea/vomiting by the patient. Such gastrointestinal problems are often experienced by terminally ill patients whose bodies are slowly deteriorating.

Parenteral administration, or, administration outside of the intestine, such as through bolus injections or slow infusions are also widely utilized. Intravenous (IV) drips are particularly popular for long-term administration of a medication in controlled dosages. However, parenteral administration is invasive and usually painful to the patient. Undesirable local reactions can occur at the site of the injection or infusion, and wheal, or skin elevation, occurs due to the injections or infusions which involve a needle and are subcutaneous, or beneath the skin. Furthermore, parenteral administration of medications may not be possible if there is a lack of peripheral vasculature and blood flow cannot move to certain areas of the body. Also, some terminally ill patients may refuse parenteral administration of medications.

Parenteral administration of medications is also not practical for long-term patient care due to the requirement that proper sites must be utilized for effective administration. Terminally ill patients may not have the physical capability of performing an injection procedure, and if physically able, may not have the knowledge to properly choose an injection site and administer the medication. Thus, while parenteral administration may be effective, a properly trained healthcare provider is usually necessary for administration. When long-term patient care must be provided by an untrained person, injection techniques may become impossible to implement, requiring a patient to stay in a hospital or other medical facility indefinitely.

Rectal administration of medication is widely used for administering a number of different medications, including non-narcotic and narcotic analgesics for pain management, antinausea medications, and steroids. However, currently available rectal administration techniques involve the use of suppositories which contain a fixed dosing of medication. The suppositories are placed within the rectum for one-time, slow, and continuous absorption. Therefore, there is generally no control over the administration rate except that provided by the fixed breakdown of the suppository and the absorption rate of the rectal mucous membrane. As such, suppositories do not provide the needed flexibility in the management of pain which often requires quick bolus administrations to combat acute pain and acute worsening of pain. Furthermore, since suppositories are generally single dose elements, extended care may require the continual insertion of single dose suppositories for continuous pain management. Such continuous monitoring is expensive and often requires a skilled caregiver when the patient is either unable or unwilling to insert the suppository.

For pain management, the intraspinal administration of non-narcotic and narcotic analgesics is important in alleviating acute and chronic pain. Approaches have been developed for delivering high concentrations of medications into the spinal cord; however, all such techniques are invasive and have associated risks related to the use of a catheter or pump for the injection or infusion. Furthermore, most of these techniques are generally expensive, as they require administration and monitoring by skilled medical personnel.

Therefore, alterative methods of administration that are less complex, demanding, and expensive, are desirable.

Recently, the use of the reversal of blood flow in the vertebral venous system or Batson's Plexus for rectal or intravenous administration of medications into selected pelvic region veins has shown promise as a method of administering analgesics and anesthetics at high concentration directly into the intraspinal areas. Reversal of flow in the Batson's Plexus refers to the physical phenomenon of reversal of blood flow in the veins of the vertebral structures when intraabdominal pressure is applied. Normally, the vertebral venous plexus in the pelvis, sacrum and lumbar spine assist in carrying the venous blood from the meningorrhachidian veins of the vertebral structures, including the spinal cord, to the sacrum and sacral plexus, the iliac veins and ultimately to the inferior vena cava and to the heart. However, the vertebral venous plexus or Batson's plexus is valveless so blood is free to flow in any direction. The Batson effect occurs upon increased intraabdominal pressure which causes reversal of pelvic and lumbar venous flow such that venous flow occurs from the sacral venous plexus and inferior vena cava into the meningorrhachidian blood vessels. In short, normal blood flow occurs from the spinal column toward the heart, but under Batson's described effect, blood flow can occur in the opposite direction, providing blood flow back to the spinal area. Using Batson's plexus reverse flow by increased intraabdominal pressure, in conjunction with the administration of analgesics using venous needle or indwelling venous catheter delivery of opioids, anesthetics or other medications into pelvic region veins that drain into the sacral plexus and Batson's plexus, the analgesic or other medication might be more efficiently and effectively administered at high concentrations to the spinal cord to alleviate pain without peripheral intravenous infusions.

Therefore, it is an objective of the present invention to administer medications to patients without the various drawbacks associated with traditional oral, rectal, and parenteral methods of administration discussed hereinabove. Furthermore, it is an objective to administer medication intravenously (IV) with greater flexibility and with central nervous system specific delivery than provided with currently available techniques.

Particularly, it is an objective of the present invention to administer non-narcotic and narcotic analgesics to continuous care and terminal patients for the management of acute and chronic pain.

It is a further objective of the present invention to administer medications in a nonpainful, noninvasive and safe way without incurring the large expense associated with procedures involving administration and continual monitoring by large numbers of skilled caretakers, such as physicians and nurses. Safe, effective and inexpensive pain management in economically depressed, third world countries is particularly important, as these countries often have large numbers of terminally ill patients without the requisite medical staff available.

It is a further objective of the present invention to provide greater flexibility in the administration of medications, both continuously and in bolus dosages and to provide for easy initiation and termination of the dispensing process.

It is a further objective of the present invention to administer medications so that the medications are rapidly and efficiently absorbed into the necessary areas of the body to alleviate the medical condition or the pain associated therewith.

It is also an objective of the present invention to more efficiently and effectively administer medications into the intraspinal area and particularly to administer anesthetics and analgesics into that area for pain management purposes.

It is also an objective of the present invention to more efficiently and effectively administer medications into the intraspinal and systemic circulation of multiple different pharmacologic agents for many different medical reasons. Medication that can be delivered by pelvic region veins and directed into the intraspinal area include any therapeutic or diagnostic agent that can be delivered by IV in any other area of the body. These include steroids, nonsteroidal anti-inflammatory agents, anti-infectives, oncolytics, immune therapies, antibleeding agents, anti-epileptic agents, fluid replacement, radiopaque x-ray imaging agents and magnetic resonance imaging agents, such as gadolinium, and radioactive diagnostic and radioactive therapeutic agents and experimental drugs (such as ziconotide, large molecules, nonpolar molecules, hormones, and immune modulating agents and other compounds, that may not or only poorly cross the blood-brain barrier, or that are poorly or nonabsorbed through the oral or rectal route) that may be useful to treat pain conditions, or hypothermia or hyperthermia therapy of the pelvic venous blood flow for therapeutic purposes.

SUMMARY OF THE INVENTION

The above-discussed objectives are addressed in the present invention which comprises an infusor system for administering medications to a patient through a venous needle or indwelling venous catheter. In a preferred embodiment of the invention, the infusor system is designed for use within the superficial to sacral venous system of a patient for administering medications into the body of the patient.

In a preferred embodiment, the infusor system comprises a needle or indwelling catheter that is placed into a superficial vein or veins of the pelvis or inguinal region including but not limited to the femoral vein, deep epigastric veins, deep circumflex iliac vein, internal iliac vein, internal pudic vein, common iliac vein, spermatic vein, dorsal vein of the penis, inguinal vein, pudendal vein, pubic veins, or genitofemoral vein. The system further comprises a delivery tube coupled at one end to a supply of liquid medication and at an opposite end to the venous needle or indwelling catheter.

The supply of medication is delivered into the tube and to the IV needle or indwelling catheter either continuously through an IV drip bag or a pump apparatus, or in a bolus dosage. To that end, the infusor system includes apparatus for coupling the IV needle or indwelling catheter to an IV bag or to a pump and also includes a bolus injection site. The infusor system further comprises a one-way valve in the delivery tube for allowing medication flow in only one direction, from the supply to the IV needle or indwelling catheter.

The infusor system eliminates the large expenses associated with other procedures which involve administration and continual monitoring by professional medical personnel. The IV needle or indwelling catheter of the infusor system may be inserted into the superficial vein or veins of the pelvis or inguinal region including, but not limited to, the femoral vein, deep epigastric veins, deep circumflex iliac vein, internal iliac vein, internal pudic vein, common iliac vein, spermatic vein, dorsal vein of the penis, inguinal vein, pudendal vein, pubic veins, or genitofemoral vein and left therein while medication is supplied. Furthermore, medication administration can be easily initiated and terminated by simply starting or stopping the flow of medication to the delivery IV needle or indwelling catheter. The infusor system provides safe, effective and inexpensive pain management and is particularly useful in economically depressed third-world countries which have large numbers of terminally ill patients who do not have the monetary resources to afford continuous attention by medical professionals, even if such professionals are available. The medications dispensed through the infusor system are rapidly and efficiently absorbed into the necessary areas of the body for alleviation of the medical condition or the pain associated therewith. Furthermore, a large number of medications, such as chemotherapy medications and some anesthetics, may be introduced through the superficial vein or veins of the pelvis or inguinal region including but not limited to the femoral vein, deep epigastric veins, deep circumflex iliac vein, internal iliac vein, internal pudic vein, common iliac vein, spermatic vein, dorsal vein of the penis, inguinal vein, pudendal vein, pubic veins, or genitofemoral vein. An IV method of use of the infusor system is particularly effective for the efficient administration of medications directly into the intraspinal area for pain management.

In an embodiment of the method of the present invention, the IV or indwelling catheter is placed within the superficial vein or veins of the pelvis or inguinal region including but not limited to the femoral vein, deep epigastric veins, deep circumflex iliac vein, internal iliac vein, internal pudic vein, common iliac vein, spermatic vein, dorsal vein of the penis, inguinal vein, pudendal vein, pubic veins, or genitofemoral vein, and medication is dispensed. Intraabdominal pressure is then increased by any number of different available methods, such as by utilizing an abdominal restraint or binder. The blood flow in the vertebral venous plexus is reversed and the dispensed medication is delivered from the rectal and sacral veins directly into the vertebral bones, the epidural and intrathecal space, and the spinal cord. By maintaining the increase in the intraabdominal pressure long enough, cranial structures will also receive the vertebral venous flow of medication.

Therefore, the infusor system of the present invention provides a more direct infusion of medication, either continuously or in bolus dosages, into the spinal cord and other vertebral structures, as compared to oral or parenteral administration, for more effective pain management. As such, analgesic medication, such as morphine, can be delivered in relatively higher concentrations to the spinal cord before circulating throughout the body and before significant dilution. Furthermore, the bypassing of liver metabolism provides a greater concentration of available medication to the necessary targeted areas. Since there are lower concentrations of the analgesics dispensed systemically within the body, side effects such as sedation, respiratory depression, nausea, and vomiting are reduced. Still further, utilizing the inventive method of the present invention, more costly injection procedures requiring skilled professionals are avoided when introducing medications within the epidural and intrathecal spaces of the spinal column.

These advantages and other advantages of the present invention will become more readily apparent below from the Brief Description of the Drawings and the Detailed Description of the Invention.

BRIEF DESCRIPTION OF THE DRAWINGS

The accompanying drawings, which are incorporated in and constitute a part of the specification, illustrate embodiments of the invention and, together with a general description of the invention given above, and the detailed description of the embodiments given below, serve to explain the principles of the invention.

DETAILED DESCRIPTION OF THE INVENTION

Figure 1:
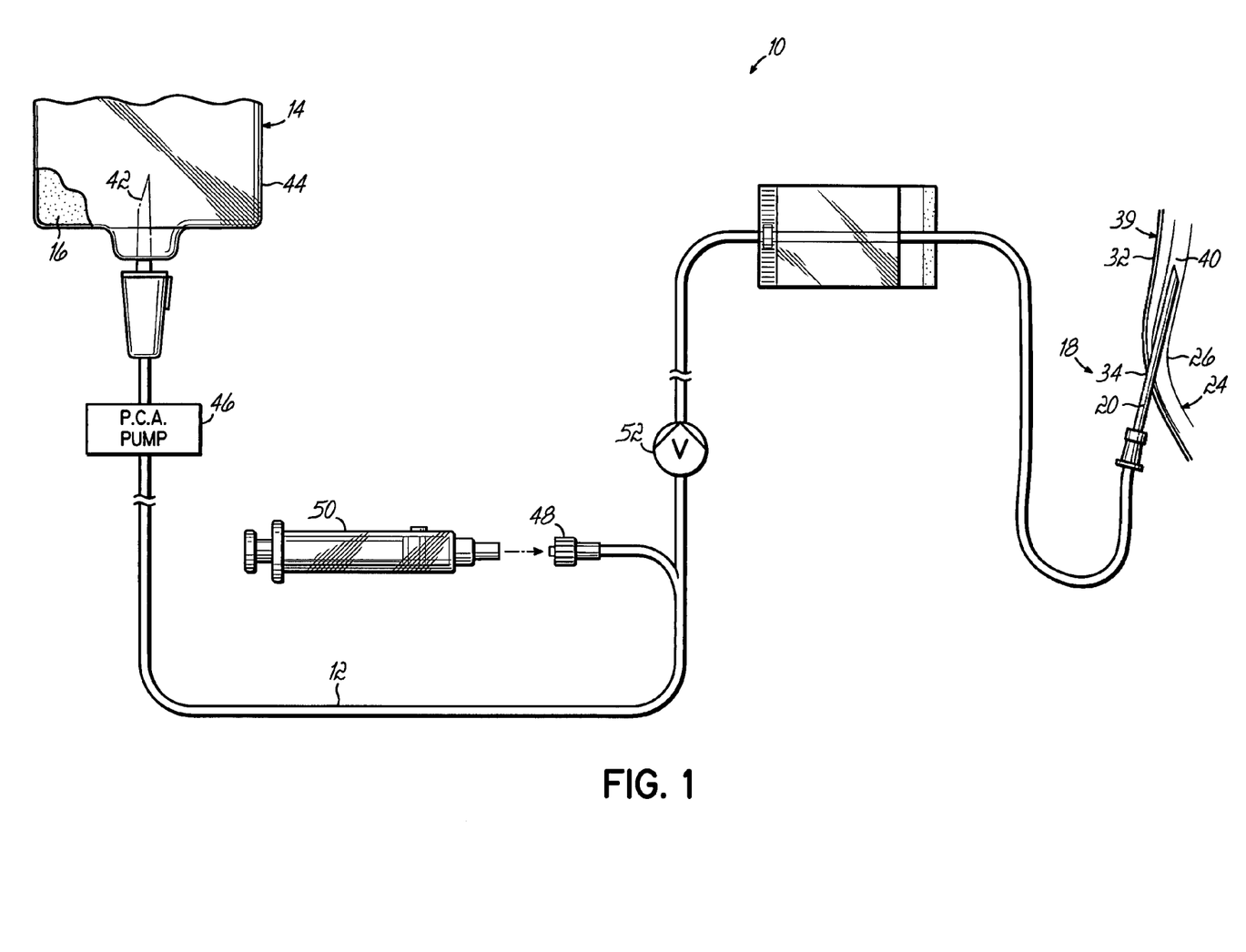
FIG. 1 is a schematic view of an embodiment of the infusor system of the present invention.

FIG. 1 is a schematic view of one embodiment of the infusor system 10 of the present invention. The infusor system 10 includes a medication delivery tube 12 which is coupled to a supply of medication 14 to be dispensed therethrough. The tube 12 may be made of PVC material or of a biodegradable material for more environmentally safe disposal. The delivery tube 12 is coupled to a delivery component 18 for dispensing medication 16 delivered thereto by the tube 12. Such a delivery component 18 may include, but is not limited to, a venous needle 20 or an indwelling venous catheter 22. As discussed further hereinbelow, the delivery component 18, such as the venous needle 20 or indwelling venous catheter 22, is operable to direct medication 16 from the tube 12 to a venous system 24 of the patient. In one embodiment, the venous system 24 may be the superficial to sacral venous system of a patient, and in particular, the medication 16 may be directed into the superficial vein or veins 26 of the pelvis 28 or inguinal region 30 of a patient.

Figure 1A:
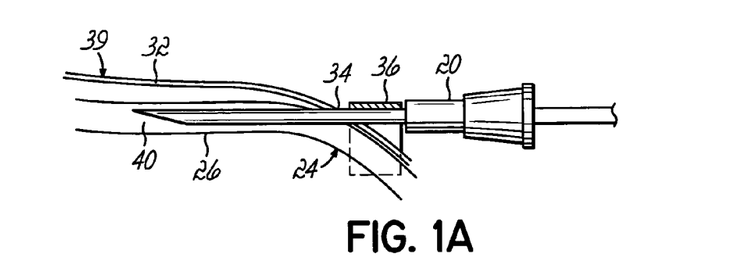
FIG. 1A is an enlarged view, in partial cross-section, of a venous needle as used in accordance with the principles of the present invention.
Figure 1B:
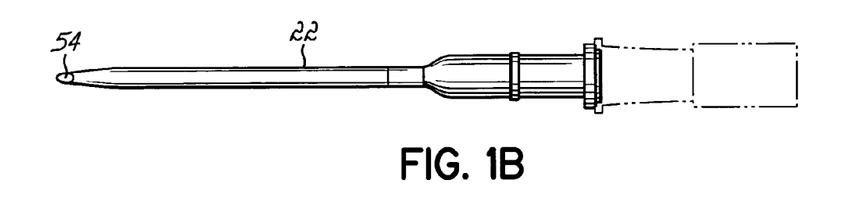
FIG. 1B is an enlarged view, in partial cross-section, of an indwelling venous catheter used in accordance with the principles of the present invention.
Figure 1C:
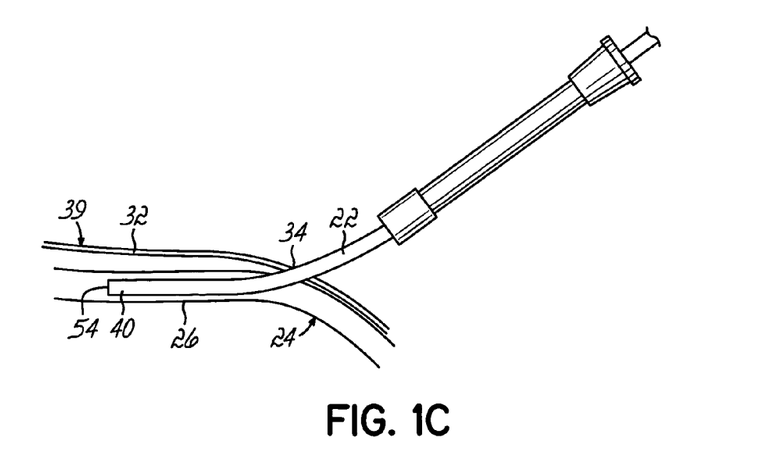
FIG. 1C is an enlarged view, partly in cross-section, of an indwelling venous catheter inserted in a vein in accordance with the principles of the present invention.

FIGS. 1A through 1C show a venous needle 20 (FIG. 1A) and an indwelling venous catheter 22 (FIGS. 1B and 1C) that may be used in the infusor system 10 of the present invention. Referring to FIG. 1A, a venous needle 20 is typically inserted into a patient with the needle 20 puncturing and protruding through the skin 32 and into the vein 26 of the patient following preparation and sterilization of the insertion site 34. Thereafter, the venous needle 20 may be held in place by a plurality of tapes 36 which hold the venous needle 20 to the insertion site 34. Referring to FIGS. 1B and 1C, an indwelling venous catheter 22 may be inserted into a vein 26 beneath the skin 32 of a patient. In particular, a venipuncture needle 38 is inserted through the skin 32 and into a vein 26, and the catheter 22 is inserted into the vein 26 through the venipuncture needle 38. Once the catheter 22 has been inserted into the vein 26, the venipuncture needle 38 used for the catheter insertion is removed, leaving the catheter 22 in the patient's vein 26.

Figure 2:
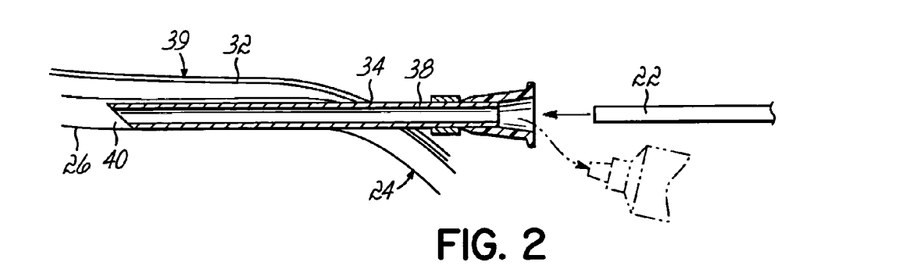
FIG. 2 is an enlarged view, partly in cross-section, showing a venipuncture needle in position in a vein and the catheter used in accordance with the principles of the present invention about to be inserted through the needle into the vein.
Figure 3:
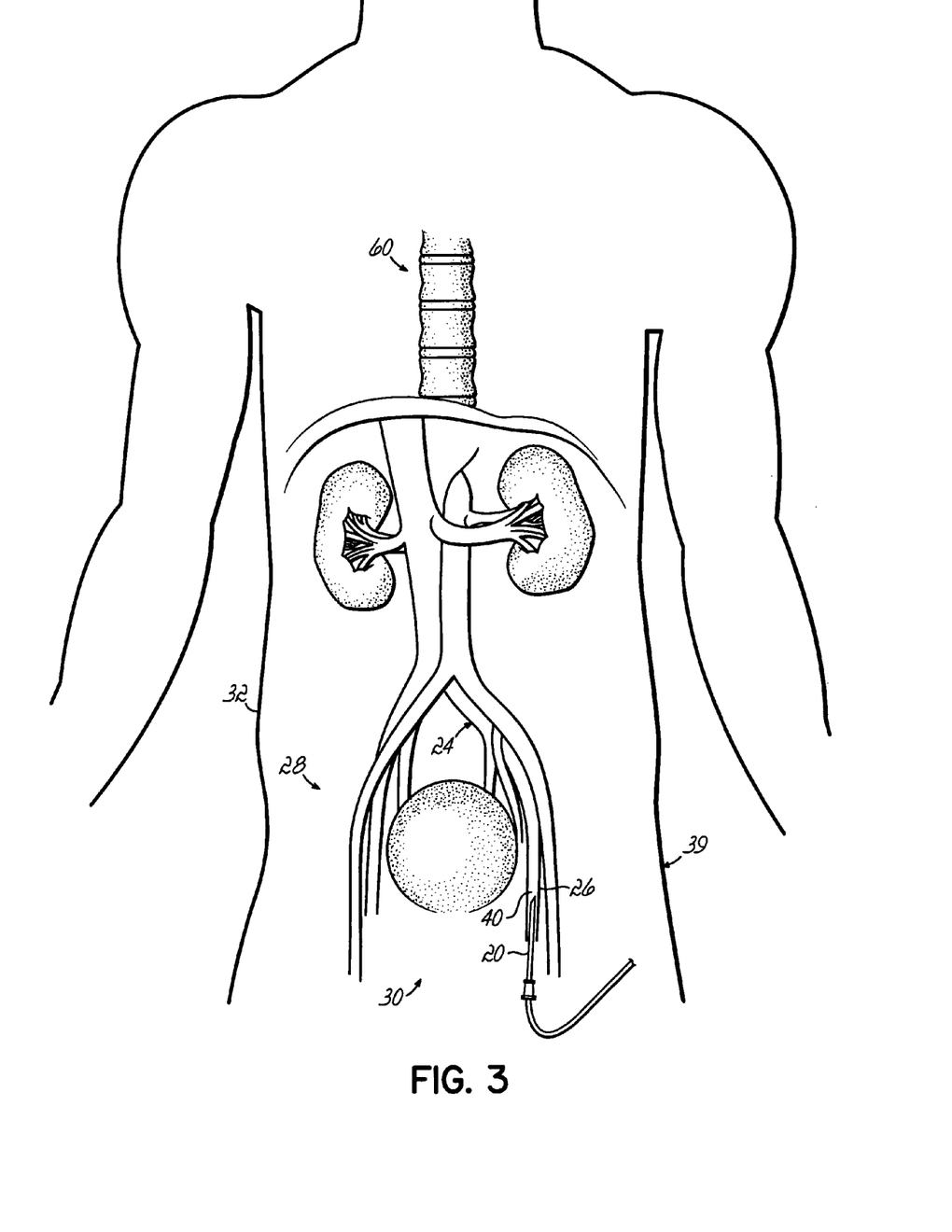
FIG. 3 is a side view, in partial cross-section, of a patient body illustrating the infusor system used within the superficial to sacral venous system of the patient.

Referring now to FIGS. 2 and 3, then delivery component 18, being an indwelling venous catheter 22 in the illustrated embodiment, is shown inserted into a portion of the superficial to sacral venous system 24 of a patient body 39. Within this venous system 24, the indwelling venous catheter 22 is able to deliver medication 16 through the tube 12 to a contact point 40. This contact point 40 may be a superficial vein or veins 26 of the pelvis 28 or inguinal region 30, including, but not limited to, the femoral vein, deep epigastric veins, deep circumflex iliac vein, internal iliac vein, pudic vein, internal pudic vein, external pudic vein, common iliac vein, spermatic vein, dorsal vein of the penis, inguinal vein, pudendal vein, pubic veins, or genitofemoral vein. It will be recognized by those of skill in the art that the contact point 40 may be in other veins 26 of the patient body 39.

As illustrated in FIG. 1, the delivery tube 12 is coupled to a medication supply 14 and delivers medication 16 to the venous needle 20 or indwelling venous catheter 22 from the supply 14. For example, a first end 42 of the delivery tube 12, being the end opposite the venous needle 20 or indwelling venous catheter 22, may be coupled to an IV drip bag 44 for continuously dispensing medications 16 at a controlled drip rate into the tube 12. Alternatively, the first end 42 of the tube 12 may be connected to a pump device 46, such as a Patient Controlled Analgesia, or PCA, pump for injecting medication 16 into the tube 12 at a predetermined pumping rate. Infusion rates and doses may be determined by a physician.

The tube 12 of the infusor system 10 of the present invention may also include a bolus injection dock 48 for receiving a syringe 50 to rapidly inject bolus dosages of medication 16 to be dispensed through the delivery component 18, such as a venous needle 20 or indwelling venous catheter 22. This may be used to alleviate acute pain or acute worsening of pain experienced by a patient utilizing the infusor system 10. If a patient is using a home infusion pump, a preset "rescue" or bolus dose is set for every time the patient or caregiver presses an extra dose/rescue button, as with other infusion pumps, as is known to those skilled in the art. A one-way valve 52 ensures that medication 16 flows in the proper direction to the venous needle 20 or indwelling venous catheter 22.

The embodiments of the infusor system 10 illustrated herein utilize venous needles 20 or indwelling venous catheters 22 which are designed and configured to be positioned within the veins 26 of the pelvis 28 or inguinal region 30. However, the infusor system 10 might also be utilized with other venous systems 24 of the body 39 which are proximal to areas requiring medication 16. For example, Batson's plexus extends up to the cervical (neck) region. Thus, a very long catheter, such as a cardiac catheter, could be extended up through the superficial pelvic veins, femoral veins, and several others, and into the vertebrovenous and meningorrhachidian vasculature (i.e. around the spinal canal and spinal cord and structures) and/or up to the base of the skull. This would allow for focal delivery and site directed delivery of medications into the higher central nervous system (CNS).

Although including an orifice 54 to direct liquid medicine from the tube 12 to the contact point 40, namely, the superficial or sacral venous system 24 of a patient, the material utilized to form the venous needle 20 or indwelling venous catheter 22 should not absorb and hold the medication 16 away from the venous system 24. Furthermore, the material should preferably not foster the growth of microfluora. While the infusor system 10 of the present invention utilizes a venous needle 20 or indwelling venous catheter 22 which is configured for remaining within a venous blood vessel 26, it may be useful to precede the insertion of the venous needle 20 or indwelling venous catheter 22 with an anesthetic to prevent reaction to the venous needle 20 or indwelling venous catheter 22 as a foreign body.

Figure 4A:
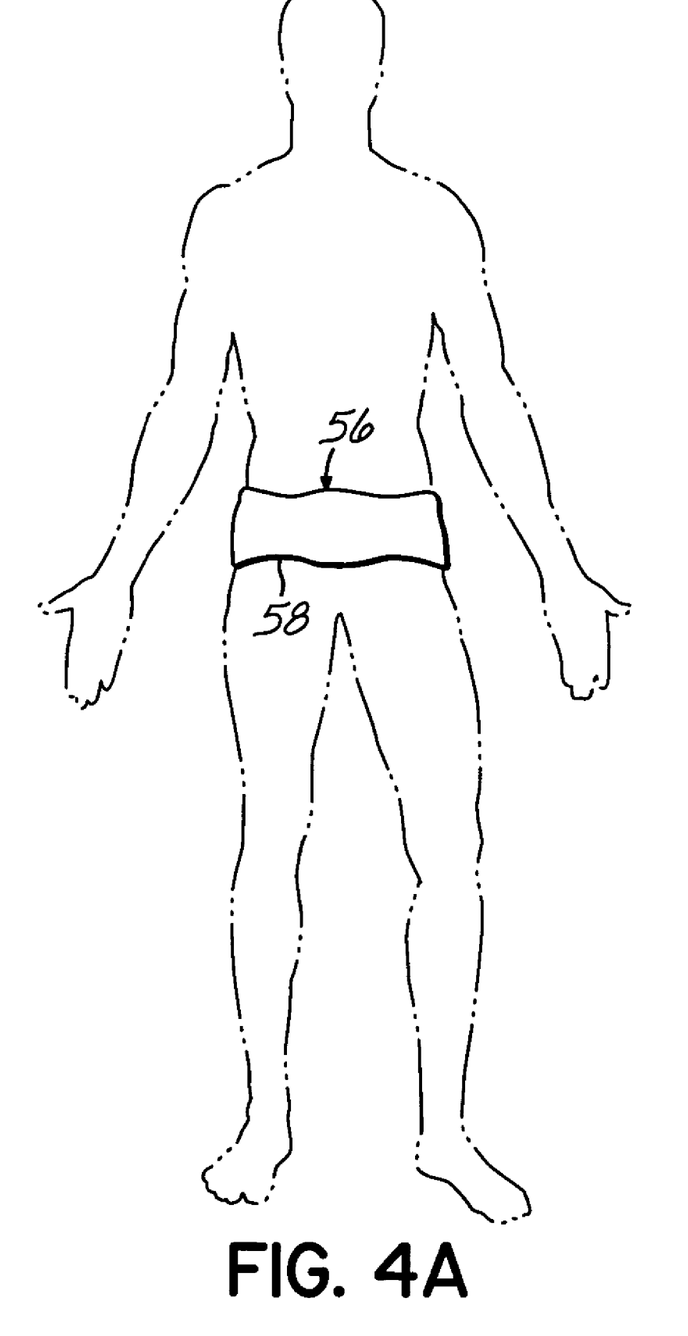
FIG. 4A is a front view of a pressure-altering device, such as an abdominal binder, of the infusor system to be utilized with the tube and catheter of the present invention.
Figure 4B:
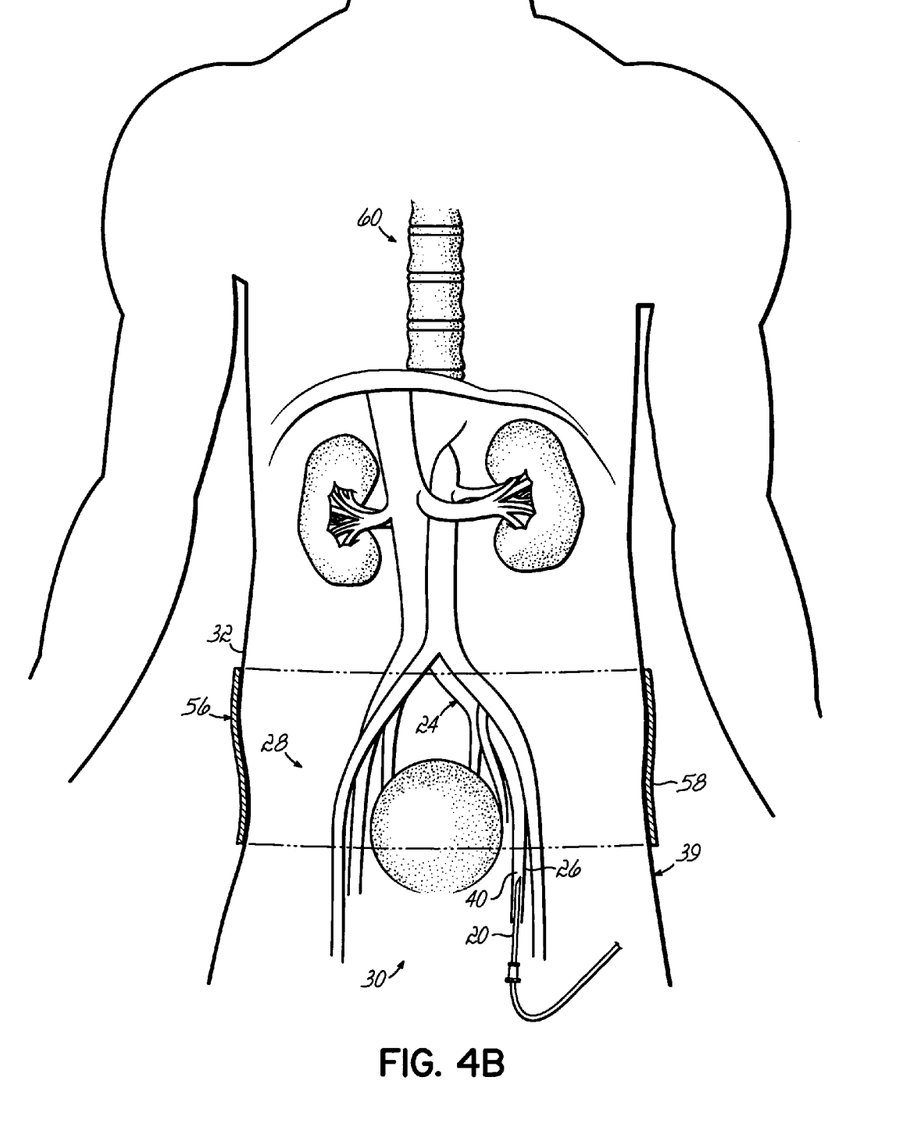
FIG. 4B is a side view of a patient's body, in partial cross-section, of a patient body, showing the pressure-altering device of the infusor system of the present invention.

Vein catheterization, in the method of the present invention, is performed by medical professionals. Likewise, a pressure-altering device 56, such as an abdominal binder 58 (FIGS. 4A and 4B), may be applied to a patient and removed from a patient by medical personnel. In some situations, the patient may be able to remove and apply the binder 58 by himself after receiving training. Additionally, in the embodiment of the present invention wherein an IV may be attached to a home infusion pump 46, such a pump 46 may also be turned on and off and bolus injections may be given by the patient, as with home infusion pumps 46 and diabetic pumps. Such pumps are commercially available from Deltec, Inc. of St. Paul, Minn. and Pharmacia of Kalamazoo, Mich. When using an abdominal binder 58 to affect reversal of flow through Batson's Plexus, the pressure applied to the binder 58 is controlled with a sphygmomanometer device or other devices, as is understood by those having skill in the relevant art. Continuous abdominal pressures to induce reversal of flow through Batson's plexus may range from about 15 mm Hg to about 150 mm Hg. Generally, obese individuals will use higher pressures, while thinner individuals will use lower pressures to induce reversal of flow through Batson's plexus.

As described previously, the delivery component 18 of the infusor system 10 may include a venous needle 20 or indwelling venous catheter 22. The venous needle 20 or indwelling venous catheter 22 preferably ranges from very small needles measuring about 25 gauge to very large needles and catheters measuring 18 gauge or larger. The delivery component 18 should sustain a flow rate of medication suitable for the application being utilized. In general, infusion rates may be as slow as "TKO", or "to keep open" rate such as 10 cc/hour (kept open by using an infusion pump), or may be relatively rapid rates of 100 cc/hr. Rapid rates may often be used in applications involving delivery of medication 16 to the central nervous system. Faster rates could be instilled depending on the medication 16 used and the need. As other examples, for morphine usage, a sustained flow rate of about 15-20 cc/hr at a morphine concentration of 5 mg/cc may be desired. Furthermore, the venous needle 20 or indwelling venous catheter 22 may have the capability of providing bolus dosage delivery of 10-20 cc/hr, either as a single dose or in multiple fractions of 20 cc/hour.

A standard intravenous catheter, such as an Angiocath®, may be used as a delivery component 18 in one particular embodiment of the present invention. This type of catheter is flexible and has a more rigid guide wire for insertion that is removed after insertion. Angiocath® catheters are commercially available from Becton, Dickinson and Company. In use, an angiocatheter, such as an Angiocath®, would be placed subcutaneously into a pelvic vein, such as a vein selected from the group described previously. Following placement of the angiocatheter, the sheath or guide wire is removed. Alternatively, a simple straight infusion needle could also be inserted into the most superficial of pelvic veins. These needles or catheters are then taped down or stitched down in the case of deep angiocatheters.

The elements of the infusor system 10 should preferably be able to withstand gamma radiation for the purpose of pre-use sterilization. Furthermore, the materials are preferably safe to use in the presence of medical diagnostic systems such as magnetic resonance imaging (MRI), x-ray, or computerized tomography (CT) scan.

Medication 16 dispensed through the venous needle 20 or indwelling venous catheter 22 is directed into the venous system 24 and distributed throughout the body 39 to address a targeted symptom or to alleviate pain experienced by the patient. Since the infusor system 10 of the invention is utilized within a venous system 24, it is noninvasive and generally nonpainful. Since no injection is involved, use of the infusor system 10 of the invention is not accompanied by the various drawbacks and side effects experienced with parenteral administration. Furthermore, the infusor system 10 may be utilized with patients who cannot tolerate orally administered medications. The infusor system 10 provides great flexibility in the dispensing of medication 16 through IV bags 44 and pumps 46. A bolus dosage of medication 16, such as a dosage of morphine for a patient suffering acute pain, can be administered through the bolus dock and received directly into blood vessels.

The infusor system 10 is safe and inexpensive. Not only will the infusor system 10 be generally inexpensive to manufacture, but it is also generally inexpensive to utilize. Once the venous needle 20 or indwelling venous catheter 22 has been properly placed, it can be left therein to provide continuous medication 16 without the need for constant medical attention, which is often associated with parenteral administered medication. Furthermore, the infusor system 10 provides continuous dispensing, unlike individual pills or suppositories that the patient or medical professional must remember to administer at predetermined intervals.

A large number of medications, such as chemotherapy, steroids, anesthetics, opioids, and other narcotic and non-narcotic analgesics may be administered using the infusor system 10 of the present invention. During operation of the infusor system 10, it is easy to initiate the administration of medication 16 simply by providing medication flow through the tube 12 and into the venous needle 20 or indwelling venous catheter 22. Similarly, stopping the medication flow will terminate the administration, whereupon it can simply be reinitiated by again beginning flow through the delivery tube 12.

In accordance with one inventive method for utilizing the infusor system 10, use of the infusor system 10 is combined with intraabdominal pressure to infuse medication 16 directly into the spinal structure 60 and the cavities surrounding the spinal structure 60. The administration of medication 16 directly into the intraspinal area, and particularly, the administration of opioids and other analgesics, is very useful for pain management. For effective intraspinal administration in accordance with the principles of the present invention, the venous needle 20 or indwelling venous catheter 22 is positioned within the superficial vein or veins 26 of the pelvis 28 or inguinal region 30 to deliver medication 16 into the superficial or sacral venous system 24. Intraabdominal pressure is then increased to create a reversal of blood flow within the vertebral venous plexus, or Batson's plexus. The intraabdominal pressure may be applied by using an abdominal restraint or abdominal binder 58 or any other medically suitable method for creating intraabdominal pressure. The intraabdominal pressure may be set for each patient and is generally not altered after the optimal pressure for full reversal of Batson's plexus flow is determined. The optimal pressure may generally be a relatively low pressure of around 60 mm Hg to 90 mm Hg, but, as will be understood by those of skill in the relevant art, with obese persons, the pressure may be higher, and in very thin persons, the pressure may be lower. The Batson's plexus is valveless, and blood is free to flow in the reverse direction when intraabdominal pressure is applied. Normally, the vertebral venous plexus in the pelvis, sacrum, and lumbar spine assist in carrying the venous blood from the meningorrhachidian veins of vertebral structures, including the spinal cord, to the sacrum and sacral plexus, the iliac veins, and ultimately, to the inferior vena cava and to the heart. However, upon reversal of pelvic, sacral, and lumbar venous flow, the venous flow occurs from the sacral venous plexus and into the meningorrhachidian blood vessels. That is, the normal blood flow that occurs from the spinal column through the sacral plexus toward the heart reverses. This reversal of flow in the Batson's plexus occurs such that blood in the sacral plexus flows back into the spinal area. Therefore, using Batson's plexus reverse flow with the infusor system 10 in accordance with the principles of the present invention, medications 16 are delivered directly into venous blood vessels 26 and more effectively and efficiently administered to the spinal cord, such as to alleviate pain. For example, morphine administered utilizing the infusor system 10 with increased intraabdominal pressure, is delivered in high concentrations to the spinal cord and other vertebral structures.

Minimal systemic dosing of morphine or other medication 16 occurs utilizing the inventive method, and thus, provides a number of distinct advantages. Concentrated medications 16, such as analgesics, are delivered into the spinal cord and other vertebral structures before circulating throughout the body 39 and before significant dilution occurs. Furthermore, the medications 16 are directly delivered into the vertebral structures 60 before liver metabolism of the medication 16 occurs. With a greater concentration of the medication 16 directed to the vertebral structures 60 instead of systemically throughout the body 39, side effects such as sedation, respiratory depression, nausea, and vomiting are reduced because there are lower concentrations of the medication 16 to the brain and brainstem. Furthermore, utilizing the inventive method, the delivery of medications 16 can be given intermittently, if desired, into the vertebral venous plexus using intermittent intraabdominal pressure, and then a systemic delivery may be initiated simply by removing the intraabdominal pressure. Therefore, high concentrations of an analgesic might be infused intraspinally to manage acute pain, and then systemically for continuous management of less acute, chronic pain. A further advantage of the inventive method is that medication 16 may be administered epidurally, that is, outside of the covering of the spinal cord, and intrathecally, that is, within the spinal fluid surrounding the spinal cord without the use of injections, which are generally costly and usually require administration by a trained anesthesiologist due to potential risks, and also require continuous monitoring by trained personnel. Therefore, the cost and the risks of effective pain management are reduced.

Drugs that are delivered intrathecally or epidurally or both, and that may now be delivered more safely, inexpensively and efficiently by reversal Batson's plexus include: chemotherapy drugs (thiotepa, methotrexate, ARA-C, steroids); antifungals (amphotericin and others); pain medications (morphine sulfate, hydromorphone, methadone, fentanyl); adjuvant analgesics (clonidine), alpha adrenergic agents; anti-spasticity drugs (baclofen); and anesthetics (bupivacaine, lidocaine, etc.).

In yet another embodiment of the present invention, the delivery tube 12 may be inserted through the pelvic veins and sacral veins and up into the vertebrovenous plexus region for aspiration or sampling of venous blood from the vertebrovenous plexus and meningorrhachidian vasculature. The purpose of the sampling of blood is to determine pathology or lack of pathology from this area of the body, such as meningitis; cell metabolism products such as lactic acid, pyruvic acid, cytokines; and biological markers such as beta-microglobulin, carcinoembryonic antigen (CEA), and other indicators of malignancies.

While the present invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A method of administering medications to a patient comprising:
   positioning a delivery component in confronting relationship with a venous blood vessel chosen from a pudic vein, an internal pudic vein, and an external pudic vein of a patient;
   increasing pressure in the body of the patient to cause reversal of blood flow in Batson's Plexus to thereby deliver medication via said reversal of blood flow; and
   delivering medication through said delivery component and into said venous blood vessel of said patient.

2. The method of claim 1, wherein said delivery component is connected to one end of a delivery tube having opposite ends, the other end of said delivery tube being couplable to a supply of liquid medication, and wherein delivering medication further comprises providing a delivery apparatus and initiating flow of medication to said tube.

3. The method of claim 2, wherein said delivery apparatus includes an injection site operatively connected to said tube, and initiating flow of medication further comprises inserting a syringe housing medication into said injection site and injecting said medication from said syringe to said tube.

4. The method of claim 2, wherein said delivery apparatus is an IV bag housing said supply of liquid medication and initiating flow of medication further comprises coupling said IV bag to said tube.

5. The method of claim 2, wherein said delivery apparatus is a pump, and initiating flow of medication further comprises operatively connecting said pump to both said tube and said supply such that said pump directs medication from said supply to said tube.

6. The method of claim 1, wherein increasing pressure in the body of a patient further comprises increasing intraabdominal pressure.

7. The method of claim 6, further comprising positioning a pressure-altering device on the patient, wherein said pressure-altering device is selected from the group consisting of an abdominal binder and an abdominal restraint.

8. The method of claim 6, further comprising increasing intraabdominal pressure to at least 30 mm Hg.

9. The method of claim 6, further comprising increasing intraabdominal pressure to a range of about 15 mm Hg to about 150 mm Hg.

10. The method of claim 1, wherein said delivery component is connected to one end of a delivery tube having opposite ends, the other end of said delivery tube being couplable to a supply of liquid medication, and further including coupling one end of said tube to said supply of liquid medication.

11. The method of claim 1, wherein said supply of liquid medication is delivered to a spinal region of the body selected from the group consisting of a vertebral bone, an epidural space, and intrathecal space, and a spinal cord.

12. The method of claim 1, wherein said delivery component is connected to one end of a delivery tube having opposite ends, the other end of said delivery tube being couplable to a supply of liquid medication, and wherein said delivery tube is further inserted up into the vertebrovenous plexus region.

13. The method of claim 12, further comprising aspirating or sampling venous blood.

\* \* \* \* \*

UNITED STATES PATENT AND TRADEMARK OFFICE
CERTIFICATE OF CORRECTION

Page 1 of 1

PATENT NO. : 7,431,717 B2
APPLICATION NO. : 10/675147
DATED : October 7, 2008
INVENTOR(S) : Gonzales It is certified that error appears in the above-identified patent and that said Letters Patent is hereby corrected as shown below:

In the Specification

Column 1,
Line 40, "are" should be --is--.

Column 2,
Line 29, "alterative" should be --alternative--.

Column 5,
Lines 48-49, "… side view of a patient's body, in partial cross-section, of a patient's body, showing…" should be --side view of a patient's body, in partial cross-section, showing…--.

Signed and Sealed this
Ninth Day of September, 2014

Michelle K. Lee
*Deputy Director of the United States Patent and Trademark Office*